(12) United States Patent
Gordon et al.

(10) Patent No.: US 9,314,553 B2
(45) Date of Patent: Apr. 19, 2016

(54) SURGICAL SYSTEM

(75) Inventors: Raphael Gordon, Ladera Ranch, CA (US); Michael D. Morgan, Costa Mesa, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 1264 days.

(21) Appl. No.: 11/972,232

(22) Filed: Jan. 10, 2008

(65) Prior Publication Data

US 2009/0182266 A1 Jul. 16, 2009

(51) Int. Cl.
*A61M 1/00* (2006.01)
*A61F 9/007* (2006.01)

(52) U.S. Cl.
CPC ........... *A61M 1/0031* (2013.01); *A61M 1/0058* (2013.01); *A61F 9/00745* (2013.01); *A61M 1/0033* (2014.02); *A61M 1/0041* (2013.01); *A61M 2205/123* (2013.01); *A61M 2205/505* (2013.01); *A61M 2210/0612* (2013.01)

(58) Field of Classification Search
CPC ........... A61M 1/0031; A61M 1/0033; A61M 1/0037; A61M 1/0041; A61M 1/0047; A61M 1/0058; A61M 1/0084; A61M 2205/505; A61M 2210/0612
USPC ........... 604/118–120; 417/44.1, 477.1, 477.2; 700/28
See application file for complete search history.

(56) References Cited

U.S. PATENT DOCUMENTS

| | | |
|---|---|---|
| 4,180,074 A | 12/1979 | Murry et al. |
| 4,493,698 A | 1/1985 | Wang et al. |
| 4,705,500 A | 11/1987 | Reimels et al. |
| 4,832,685 A | 5/1989 | Haines |
| 4,935,005 A | 6/1990 | Haines |
| 5,265,638 A * | 11/1993 | Fischer et al. ............... 137/103 |
| 5,267,956 A | 12/1993 | Beuchat |
| 5,342,293 A | 8/1994 | Zanger |
| 5,364,342 A | 11/1994 | Beuchat et al. |
| 5,380,280 A | 1/1995 | Peterson |
| 5,499,969 A | 3/1996 | Beuchat et al. |
| 5,556,378 A | 9/1996 | Storz et al. |
| 5,569,188 A | 10/1996 | Mackool |
| 5,586,973 A | 12/1996 | Lemaire et al. |
| 5,674,194 A | 10/1997 | Jung et al. |
| 5,676,650 A | 10/1997 | Grieshaber et al. |
| 5,693,013 A * | 12/1997 | Geuder .......................... 604/35 |
| 5,747,824 A | 5/1998 | Jung et al. |
| 5,836,909 A | 11/1998 | Cosmescu |
| 5,899,674 A | 5/1999 | Jung et al. |
| 6,106,512 A | 8/2000 | Cochran et al. |
| 6,251,113 B1 | 6/2001 | Appelbaum |

(Continued)

FOREIGN PATENT DOCUMENTS

| | | |
|---|---|---|
| EP | 0717970 | 6/1996 |
| EP | 1310267 | 5/2003 |

(Continued)

OTHER PUBLICATIONS

International Searching Authority, International Search Report, PCT/US2009/030392, May 5, 2009, (4 pages).

(Continued)

*Primary Examiner* — Bhisma Mehta
*Assistant Examiner* — Larry R Wilson

(57) ABSTRACT

A surgical system with a variable controller that allows the user to selectively vary the level of venting performance.

1 Claim, 2 Drawing Sheets

(56) References Cited

U.S. PATENT DOCUMENTS

| | | |
|---|---|---|
| 6,261,283 B1 | 7/2001 | Morgan et al. |
| 6,299,591 B1 | 10/2001 | Banko |
| 6,632,214 B2 | 10/2003 | Morgan et al. |
| 6,740,074 B2 | 5/2004 | Morgan et al. |
| 6,962,488 B2 | 11/2005 | Davis et al. |
| 2002/0045887 A1 | 4/2002 | DeHoogh |
| 2003/0073980 A1 | 4/2003 | Finlay et al. |
| 2003/0225366 A1 | 12/2003 | Morgan et al. |
| 2004/0253129 A1 | 12/2004 | Sorenson et al. |
| 2006/0078448 A1* | 4/2006 | Holden ............... 417/477.2 |
| 2006/0224116 A1 | 10/2006 | Underwood et al. |
| 2006/0248477 A1 | 11/2006 | Boukhny et al. |
| 2008/0004728 A1 | 1/2008 | Essex et al. |
| 2008/0125697 A1 | 5/2008 | Gao |
| 2009/0018488 A1 | 1/2009 | Davis et al. |
| 2009/0049397 A1 | 2/2009 | Boukhny |

FOREIGN PATENT DOCUMENTS

| | | |
|---|---|---|
| JP | 07-000442 | 6/1995 |
| JP | 11-206803 | 8/1999 |
| JP | 11-244321 | 9/1999 |
| JP | 2001-79031 | 3/2001 |
| JP | 2003-210512 | 7/2003 |
| WO | WO 9218049 | 10/1992 |
| WO | WO 98/08442 | 3/1998 |
| WO | WO 02/32354 | 4/2002 |
| WO | WO 2005/061025 | 7/2005 |
| WO | 2006/101908 A2 | 9/2006 |
| WO | 2009/089319 A1 | 7/2009 |

OTHER PUBLICATIONS

International Searching Authority, Written Opinion of the International Searching Authority, PCT/US2009/030392, May 5, 2009, (6 pages).

Becher, Claus Thomas, Notice of Opposition and EPO Communication (D1, D1.1.1, D1.1.2, D1.1.3, D1.2, and D1.3 provided below), EP2229194B1, Mar. 20, 2013, 47 pages.

D1 AMO Advanced Medical Optics, Inc., "Z370101 Rev 04, "Whitestar SignatureTM Owner's and Operator's Manual"" AMO Advanced Medical Optics, Inc., Jun. 6, 2007.

D1.1.1 Invoice No. 1022137204 to Dupage Medical Group, Ltd., Oct. 23, 2007.

D1.1.2 Invoice No. 1022172080 to Swedish Covenant Hospital, Nov. 13, 2007.

D1.1.3 Invoice No. 1022207218 to SCA-Northwest Surgicare, Dec. 6, 2007.

D1.2 Printouts from document control system Agile, Feb. 1, 2011.

D1.3 Page from Opponent's documents of the quality system operating procedure relating to an entry in D1.2, Received Mar. 20, 2013.

Prosecution History of EP Patent Application No. 09700260.4 (including Opposition Proceedings and references) downloaded Sep. 22, 2015, Grant No. EP2229194, granted Jun. 20, 2012, 416 pgs.

* cited by examiner

SURGICAL SYSTEM

BACKGROUND OF THE INVENTION

This invention relates generally to the field of cataract surgery and more particularly to a method of operating a surgical system or console.

The human eye in its simplest terms functions to provide vision by transmitting light through a clear outer portion called the cornea, and focusing the image by way of the lens onto the retina. The quality of the focused image depends on many factors including the size and shape of the eye, and the transparency of the cornea and lens.

When age or disease causes the lens to become less transparent, vision deteriorates because of the diminished light which can be transmitted to the retina. This deficiency in the lens of the eye is medically known as a cataract. An accepted treatment for this condition is surgical removal of the lens and replacement of the lens function by an artificial intraocular lens (IOL).

In the United States, the majority of cataractous lenses are removed by a surgical technique called phacoemulsification. During this procedure, a thin phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens.

A typical ultrasonic surgical device suitable for ophthalmic procedures consists of an ultrasonically driven handpiece, an attached cutting tip, and irrigating sleeve and an electronic control console. The handpiece assembly is attached to the control console by an electric cable and flexible tubings. Through the electric cable, the console varies the power level transmitted by the handpiece to the attached cutting tip and the flexible tubings supply irrigation fluid to and draw aspiration fluid from the eye through the handpiece assembly.

The operative part of the handpiece is a centrally located, hollow resonating bar or horn directly attached to a set of piezoelectric crystals. The crystals supply the required ultrasonic vibration needed to drive both the horn and the attached cutting tip during phacoemulsification and are controlled by the console. The crystal/horn assembly is suspended within the hollow body or shell of the handpiece by flexible mountings. The handpiece body terminates in a reduced diameter portion or nosecone at the body's distal end. The nosecone is externally threaded to accept the irrigation sleeve. Likewise, the horn bore is internally threaded at its distal end to receive the external threads of the cutting tip. The irrigation sleeve also has an internally threaded bore that is screwed onto the external threads of the nosecone. The cutting tip is adjusted so that the tip projects only a predetermined amount past the open end of the irrigating sleeve.

In use, the ends of the cutting tip and irrigating sleeve are inserted into a small incision of predetermined width in the cornea, sclera, or other location. The cutting tip is ultrasonically vibrated along its longitudinal axis within the irrigating sleeve by the crystal-driven ultrasonic horn, thereby emulsifying the selected tissue in situ. The hollow bore of the cutting tip communicates with the bore in the horn that in turn communicates with the aspiration line from the handpiece to the console. A reduced pressure or vacuum source in the console draws or aspirates the emulsified tissue from the eye through the open end of the cutting tip, the cutting tip and horn bores and the aspiration line and into a collection device. The aspiration of emulsified tissue is aided by a saline flushing solution or irrigant that is injected into the surgical site through the small annular gap between the inside surface of the irrigating sleeve and the cutting tip. Once the hard parts of the lens is emulsified and removed, the ultrasonic cutting step is typically followed by Irrigation/Aspiration (I/A) step that removes the softer lens material by aspirating only.

While the fragments of the material to be aspirated are reduced to the size which may flow uninhibited through tip of the handpiece, occasionally they block the aspiration port without going though. In these cases the user typically vents (i.e. releases vacuum from the aspiration line). The act of venting allows user to release the blocking fragment, so he/she can reposition it, to attempt further aspiration. Also in some instances, the aspiration port may accidentally capture a tissue that was not intended for aspiration, such as iris or posterior capsule. In these cases the user employs venting as well, to release the captured tissue to prevent tissue damage.

Venting process typically involves opening a vent valve to release vacuum and bringing system pressure to vent source pressure. Depending on the venting system type (fluid or air vented) the vent source pressure would vary. For example air vented system would vent to the ambient pressure (i.e. 0.) A liquid venting system may vent to the irrigation bottle, i.e. to the hydrostatic pressure that is function of the bottle height. Also, some instruments may utilize different or additional methods of venting, such as aspiration pump reversal. In all cases, the system pressure is automatically brought to a fixed level determined by the system design.

While fixed pressure venting typically accomplishes the task, wide variety of the modern phaco tips and accessories, as well as wide range of a modern system settings (such bottle height and vacuum limit), can affect the consistency of the venting action user gets. In addition, a variety of evolved user techniques contributes to the variability of the vent performance. For example, a certain user technique can result in under-venting, forcing user to use reflux more often. In other cases, a user technique can be prone to over-venting, resulting in excessive lens material regurgitation. Depending upon the surgical technique being employed, this automatic operation can result to too much or too little vacuum being vented. This is particularly true with the large number of different types of tips, techniques and accessories currently available.

Therefore, a need continues to exist for a method of variably controlling aspiration venting on surgical consoles.

BRIEF SUMMARY OF THE INVENTION

The present invention improves upon the prior art by providing a surgical system with a variable controller that allows the user to selectively vary the level of venting performance. Accordingly, one objective of the present invention is to provide a surgical console control system.

Another objective of the present invention is to provide a surgical console control system allowing the user to adjust or control the venting operation.

These and other advantages and objectives of the present invention will become apparent from the detailed description and claims that follow.

DETAILED DESCRIPTION OF THE INVENTION

System 10 of the present invention generally includes surgical console 12 and cassette 14. Console 12 may be any suitably modified commercially available surgical console, such as the INFINITI® Vision System available from Alcon Laboratories, Fort Worth, Tex. Cassette 14 may be any suitably modified commercially available surgical cassettes, such as those described in U.S. Pat. Nos. 5,267,956, 5,364,342 and 5,499,969 (Beuchat, et al.), U.S. Pat. No. 5,899,674 (Jung, et al.) or U.S. Pat. No. 6,962,488 B2 (Davis, et al.). Cassette 14 is held in operative association with console 12 by means well-known in art.

Figure 1:
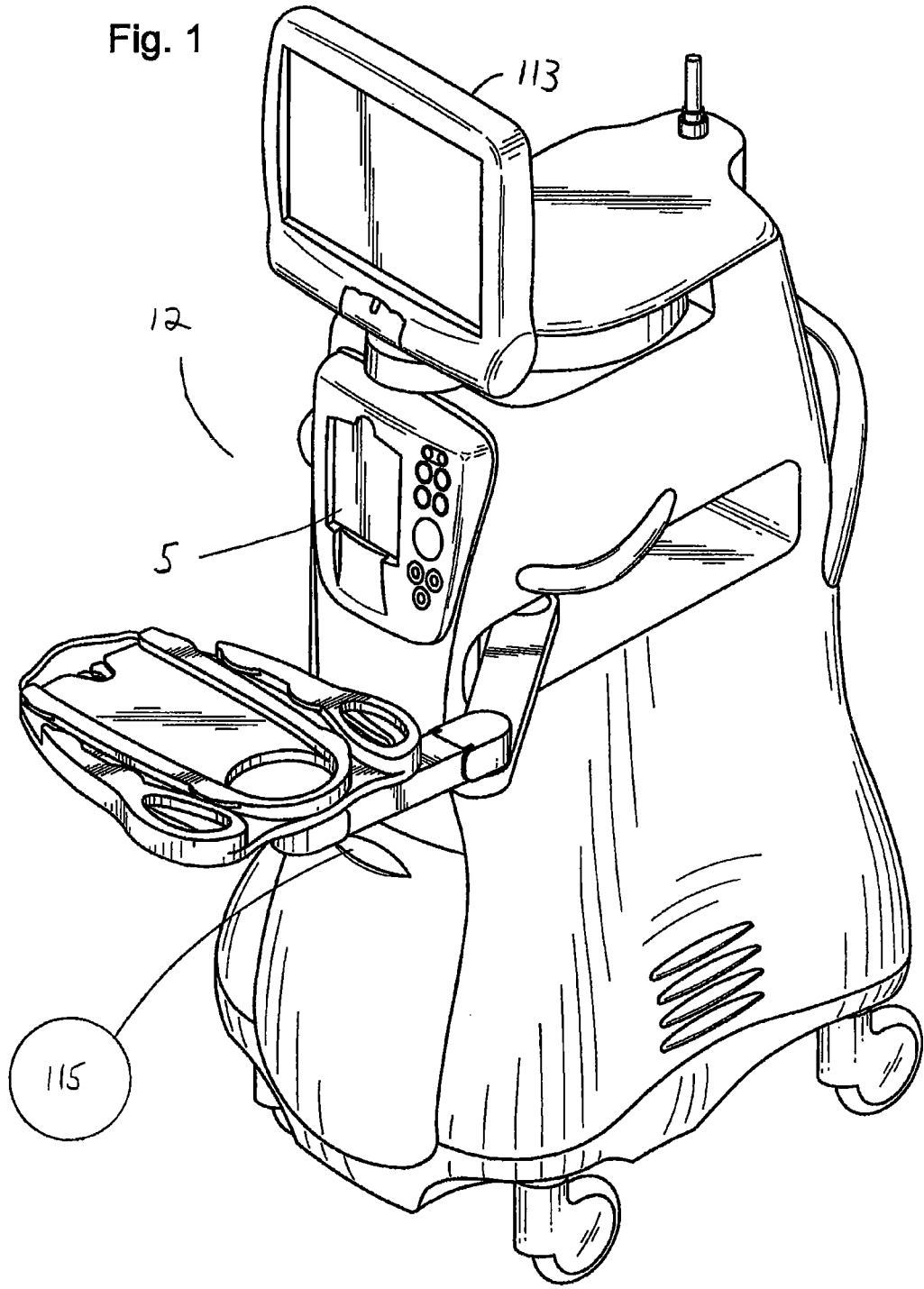
FIG. 1 is a perspective view of an exemplary surgical control console that may be used with the present invention.
Figure 2:
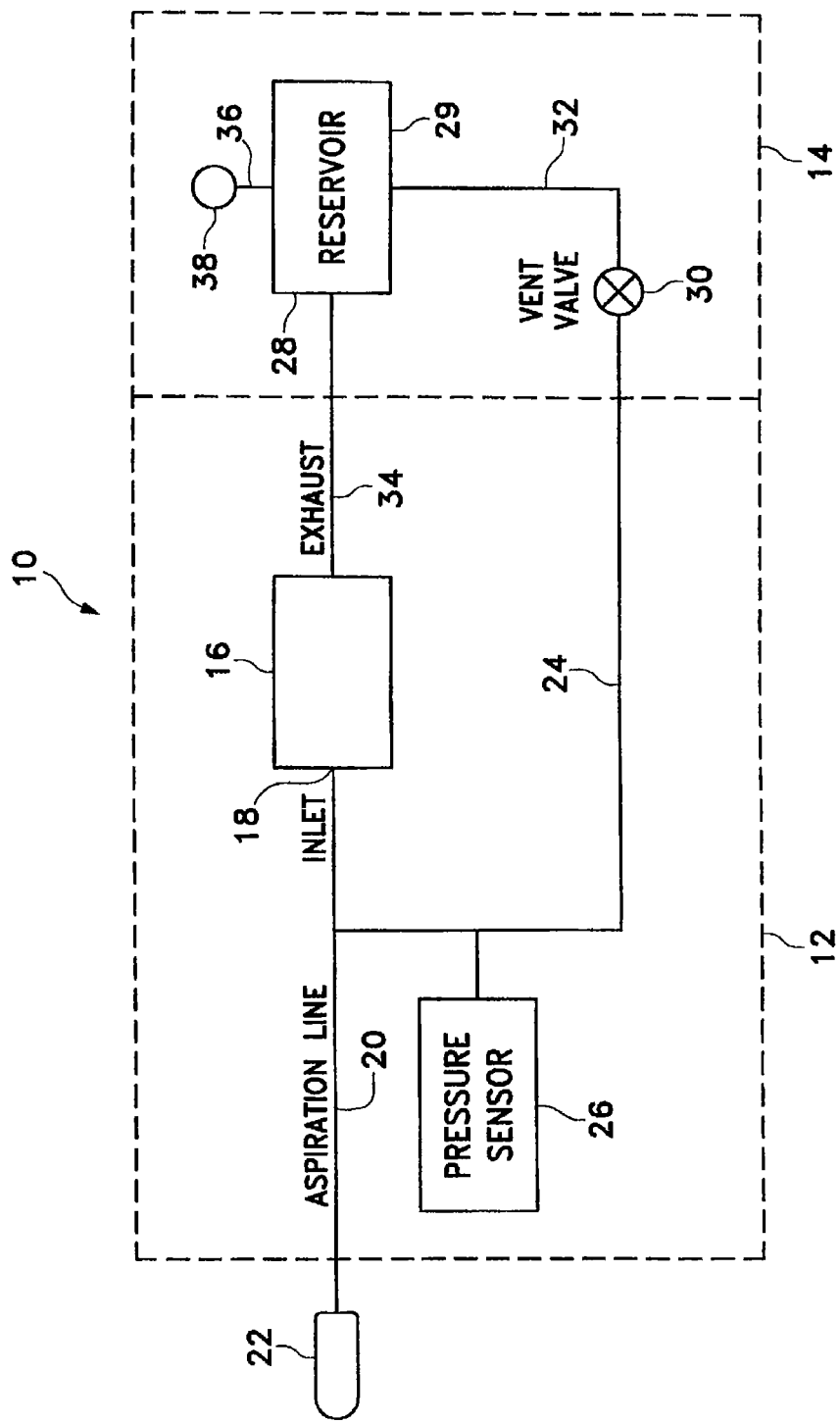
FIG. 2 is a schematic illustration of a system and cassette that can be used with the present invention.

As seen in FIG. 2, console 12 generally contains aspiration pump mechanism 16, which may be any suitable flow or vacuum based pump, such pumps being widely known in the art. For example, pump mechanism 16 may be a peristaltic pump roller head that interacts with a peristaltic pump tube formed by aspiration line 20 and aspiration exhaust line 34. Aspiration line 20 is connected to surgical handpiece 22 on one end and end 18 of aspiration line 20 opposite handpiece 22 interacts with pump mechanism 16 so as to draw fluid through handpiece 22 thereby providing handpiece 22 with an aspiration function. Aspiration line 20 is intersected between handpiece 22 and 18 by aspiration vent line 24. In fluid communication with aspiration vent line 24 is pressure sensor 26, which may be one of a variety of invasive or non-invasive pressure sensors well-known in the art.

Cassette 14 generally contains fluid reservoir 28. Extending from reservoir 28 at or near bottom 29 is aspiration vent line 32, which fluidly connects to aspiration vent line 24 through vent valve 30. Aspirant or exhaust from pump mechanism 16 is directed into reservoir 28 through aspiration exhaust line 34. Reservoir 28 may also vent to ambient through reservoir vent line 36 which may contain antimicrobial filter 38.

As discussed above, while it is preferred that pump mechanism 16 be a peristaltic roller head and that aspiration line 20 and aspiration exhaust line 34 be formed in one continuous length so as to form a peristaltic pump tube that interacts with pump mechanism 16, one skilled in the art will recognize that aspiration line 20 and aspiration exhaust line 34 may be formed as a separate piece or pieces or may be formed integrally with cassette 14 and that pump mechanisms 16 other than peristaltic pump roller heads may be used, such as linear peristaltic pumps.

In addition, pressure sensor 26 is depicted as being contained within console 12. One skilled in the art will recognize that portions of pressure sensor 26, such as a pressure diaphragm (not shown) may be contained in or on cassette 14 and interact with a force transducer or other means (not shown) contained within console 12.

In use, cassette 14 is installed on or within console 12 and held in operative association with console 12 in cassette receiving area 5 of console 12 by means well-known in the art. System 10 is primed initially with clean surgical fluid so that a small amount of fluid fills reservoir 28. During surgery, pump mechanism 16 draws aspirant through handpiece 22 and into reservoir 28. If the vacuum within aspiration line 20 is too high and needs to be vented, vent valve 30 is opened allowing aspirant to be drawn from reservoir 28 at or near bottom 29 (reservoir 28 being at or near ambient) and into aspiration line 20 (which contains a vacuum) through aspiration vent line 24. One skilled in the art will recognize that by varying the vertical position of reservoir 28 relative to aspiration line 20, various vent head pressures may be achieved. In addition, pump 16 may also be reversed, while monitoring pressure sensor 26, so as to pressurize aspiration line 20 and thereby help reduce the vacuum in aspiration line 20 in an expeditious manner.

The present invention includes allowing the user to adjust the venting operation of vent valve 30 and pump 16. Such adjustment can be made through any of a variety of input devices or mechanisms normally found on commercially available surgical consoles, such as touch screen 113 on console 12 or footswitch 115 connected to control console 12, by software commands well within the capabilities of one skilled in the art. Such adjustments may be made in any of a number of ways, such as varying the timing of the operation vent valve 30, variably changing the requested drop in vacuum or varying the amount of aspiration fluid displaced. In addition, system 10 can contain pre-programmed "levels" of venting adjustment (e.g., aggressive, moderate, mild), with the user selecting a desired level.

This description is given for purposes of illustration and explanation. It will be apparent to those skilled in the relevant art that changes and modifications may be made to the invention described above without departing from its scope or spirit.

We claim:

1. A surgical system, comprising:
a surgical handpiece having an aspiration function;
a control console;
an aspiration pump at least partially located in the control console, the aspiration pump providing vacuum to the surgical handpiece through an aspiration line;
an aspiration vent in the aspiration line between the handpiece and the pump;
a reservoir coupled to the aspiration vent; and
a user input device coupled to the control console, the user input device comprising a touchscreen and/or a keyboard for receiving user input, wherein the user input comprises a venting parameter for the aspiration pump or the aspiration vent, and wherein the system is configured to vary the venting parameter of the aspiration vent or the aspiration pump according to the received user input, wherein the venting parameter is directly related to performance of the aspiration pump or the aspiration vent during a venting event;
wherein the user input comprises a requested amount of aspiration fluid to displace and wherein varying the venting parameter of the aspiration vent comprises opening the vent until the requested amount of aspiration fluid has been displaced from the reservoir.

* * * * *